United States Patent
Hunt

(10) Patent No.: US 10,430,936 B2
(45) Date of Patent: *Oct. 1, 2019

(54) ACTIVE REAL-TIME CHARACTERIZATION SYSTEM FOR IDENTIFYING SURFACE CONTAMINATION

(71) Applicant: The Boeing Company, Chicago, IL (US)

(72) Inventor: Jeffrey H. Hunt, Thousand Oaks, CA (US)

(73) Assignee: The Boeing Company, Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/902,076

(22) Filed: Feb. 22, 2018

(65) Prior Publication Data

US 2019/0259147 A1  Aug. 22, 2019

(51) Int. Cl.
| | | |
|---|---|---|
| *G06T 7/00* | (2017.01) | |
| *H04N 5/225* | (2006.01) | |
| *H04N 5/247* | (2006.01) | |
| *H04N 5/33* | (2006.01) | |

(52) U.S. Cl.
CPC ......... *G06T 7/0004* (2013.01); *H04N 5/2256* (2013.01); *H04N 5/247* (2013.01); *H04N 5/332* (2013.01); *G06T 2207/10048* (2013.01); *G06T 2207/10152* (2013.01)

(58) Field of Classification Search
CPC combination set(s) only.
See application file for complete search history.

(56) References Cited

U.S. PATENT DOCUMENTS

| | | | | |
|---|---|---|---|---|
| 4,639,923 A | | 1/1987 | Tang | |
| 5,710,429 A | * | 1/1998 | Alfano et al. | ......... G01N 21/49 250/330 |
| 5,973,778 A | | 10/1999 | Hunt | |

(Continued)

FOREIGN PATENT DOCUMENTS

EP   2982947 A1   2/2016

OTHER PUBLICATIONS

Extended European Search Report dated Jun. 26, 2019 issued in corresponding EP Application No. EP19158906, 9 pgs.

*Primary Examiner* — Janese Duley
(74) *Attorney, Agent, or Firm* — Toler Law Group, PC

(57) ABSTRACT

An active real-time characterization system for identifying the presence of surface contaminants on to an outer surface of an article under test. Infrared and visible light sources controllably output a beam of coherent light directed at a particular area on the article under test, the infrared light source having an optical parametric oscillator coupled to an optical parametric amplifier. A series of cameras, including a visible light camera, a visible light second harmonic generation camera, an infrared camera, an infrared second harmonic generation camera, a sum-frequency camera and a third-order camera each include an associated filter system and are each configured to receive return beams of light at predetermined frequencies controlled by the filter system. A processor determines whether the received signals have a spectral response that is different from a baseline spectral response thereby indicating that contaminants exist on the surface of the article under test.

20 Claims, 4 Drawing Sheets

(56) References Cited

U.S. PATENT DOCUMENTS

| | | |
|---|---|---|
| 6,781,686 B2 | 8/2004 | Hunt |
| 6,788,405 B2 | 9/2004 | Hunt |
| 6,795,175 B2 | 9/2004 | Hunt |
| 6,798,502 B2 | 9/2004 | Hunt |
| 6,819,844 B2 | 11/2004 | Hunt |
| 7,289,656 B2 * | 10/2007 | Engelbart ............. G01N 21/95 |
| | | 382/141 |
| 7,304,305 B2 | 12/2007 | Hunt |
| 7,757,558 B2 | 7/2010 | Bossie et al. |
| 7,983,469 B2 | 7/2011 | Engelbart et al. |
| 8,664,583 B2 | 3/2014 | Hunt et al. |
| 8,789,837 B2 | 7/2014 | Chang et al. |
| 9,996,765 B2 * | 6/2018 | Yajko ........................ G06T 7/90 |
| 2003/0218740 A1 | 11/2003 | Hunt |
| 2003/0231302 A1 * | 12/2003 | Hunt ..................... G01N 21/94 |
| | | 356/237.2 |
| 2013/0048841 A1 | 2/2013 | Hunt et al. |
| 2013/0050685 A1 | 2/2013 | Hunt et al. |
| 2016/0116401 A1 | 4/2016 | Hunt |
| 2016/0119557 A1 | 4/2016 | Hunt |
| 2017/0132799 A1 * | 5/2017 | Yajko ........................ G06T 7/90 |

* cited by examiner

ACTIVE REAL-TIME CHARACTERIZATION SYSTEM FOR IDENTIFYING SURFACE CONTAMINATION

FIELD

This disclosure relates generally to an active real-time characterization system that surface contamination on articles being manufactured.

BACKGROUND

During the manufacture of a parts for use in a larger assembly, contaminants such as particulates or thin films may exist on the surface of the part being formed. The existence of such contaminants can be extremely difficult to monitor. Existing solutions typically rely on certain procedures used to remove such contamination but without any direct measurements ensuring that the contamination has actually been removed.

Accordingly, there is a need for a monitoring system which addresses the drawbacks identified above.

SUMMARY

In a first aspect, an active real-time characterization system for identifying the presence of contaminants on an outer surface of an article under test includes an infrared light source for outputting a beam of coherent infrared light. The infrared light source includes an optical parametric oscillator coupled to an optical parametric amplifier. The infrared light source is configured to direct the beam of coherent infrared light at a particular area on the article under test. A first visible light source outputs a first beam of coherent visible light. The first visible light source is configured to direct the first beam of coherent visible light at the same particular area on the article under test. A visible light camera and a visible light second harmonic generation camera are each configured to receive a first predetermined return beam of light from the particular area on the article under test. Each of the visible light camera and visible light second harmonic generation camera has a filter system that passes only light of a predetermined frequency to an associated one of the visible light camera and visible light second harmonic generation camera. An infrared camera and an infrared second harmonic generation camera are each configured to receive a second predetermined return beam of light from the particular area on the article under test. Each of the infrared camera and infrared second harmonic generation camera has an associated filter system that passes only light of a predetermined frequency to an associated one of the infrared camera and infrared second harmonic generation camera. A sum-frequency camera is configured to receive a third return beam of light from the particular area on the article under test. The sum-frequency camera has an associated filter system that passes only light of a predetermined frequency to the sum-frequency camera. A processor is coupled to receive signals from the visible light camera, the visible light second harmonic generation camera, the infrared camera, the infrared second harmonic generation camera and the sum-frequency camera. The processor is configured to process the received signals to determine whether the received signals have a spectral response that is different from a baseline spectral response thereby indicating that contaminants exist on the surface of the article under test.

In one further embodiment, the active real-time characterization system may have a second visible light source for outputting a second beam of coherent visible light. The second visible light source may be configured to direct the second beam of coherent visible light at the same particular area on the article under test. A third-order camera may be configured to receive a fourth return beam of light from the particular area on the article under test. The third-order camera may have a filter system a filter system that passes only light of a predetermined frequency to the third-order camera. The processor may be configured to receive signals from the third-order camera and to process the signals from the third-order camera in addition to the signals from the visible light camera, the visible light second harmonic generation camera, the infrared camera, the infrared second harmonic generation camera and the sum-frequency camera to determine whether the received signals have a spectral response that is different from a baseline spectral response thereby indicating that contaminants exist on the surface of the article under test.

In another further embodiment, each of the light sources may include an intensity control for setting a predetermined intensity for a respective output beam of coherent light. Further, each of the light sources may include a frequency control for setting a predetermined wavelength for a respective output beam of coherent light. Still further, each of the light sources may include a polarization control for setting a predetermined polarization for a respective output beam of coherent light. In addition, each of the cameras may include an intensity control for setting a predetermined intensity for a respective input beam of light. Also, each of the cameras may include a frequency control for setting a predetermined wavelength for a respective input beam of light. Yet further, each of the cameras may include a polarization control for setting a predetermined polarization for a respective input beam of light. Finally, the active real-time characterization system may further include a beam splitter configured to split a return beam of light into two portions, a first portion directed to the visible light camera and a second portion directed to the visible light second harmonic generation camera.

In a second aspect, an active real-time characterization system for identifying the presence of contaminants on an outer surface of an article under test includes an infrared light source for outputting a beam of coherent infrared light. The infrared light source includes an optical parametric oscillator coupled to an optical parametric amplifier. The infrared light source is configured to direct the beam of coherent infrared light at a particular area on the article under test. A first visible light source outputs a first beam of coherent visible light. The first visible light source is configured to direct the first beam of coherent visible light at the same particular area on the article under test. A visible light camera and a visible light second harmonic generation camera are each configured to receive a first predetermined return beam of light from the same particular area on the article under test. Each of the visible light camera and visible light second harmonic generation camera has a filter system that passes only light of a predetermined frequency to an associated one of the visible light camera and visible light second harmonic generation camera. An infrared camera and an infrared second harmonic generation camera are each configured to receive a second predetermined return beam of light from the same particular area on the article under test. Each of the infrared camera and infrared second harmonic generation camera has a filter system an associated filter system that passes only light of a predetermined frequency to an associated one of the infrared camera and infrared second harmonic generation camera. A processor is coupled to receive signals from the visible light camera, the visible light second harmonic generation camera, the infrared camera, and the infrared second harmonic generation camera. The processor is configured to process the received signals to determine whether the received signals have a spectral response that is different from a baseline spectral response thereby indicating that contaminants exist on the surface of the article under test.

In a further embodiment, the active real-time characterization system may include a second visible light source for controllably outputting a second beam of coherent visible light. The second visible light source may be configured to direct the second beam of coherent visible light at the same particular area on the article under test. A sum-frequency camera may be configured to receive a fourth return beam of light from the particular area on the article under test. The sum-frequency camera may have an associated filter system that passes only light of a predetermined frequency to the sum-frequency camera. Finally, the processor may be configured to receive signals from the sum-frequency camera and to process the signals from the sum-frequency camera in addition to the signals from the visible light camera, the visible light second harmonic generation camera, the infrared camera, and the infrared second harmonic generation camera to determine whether the received signals have a spectral response that is different from a baseline spectral response thereby indicating that contaminants exist on the surface of the article under test.

In a third aspect, a method identifies the presence of surface contaminants on to an outer surface of an article under test. First, light beams are generated from a first visible light source and an infrared light source comprising an optical parametric oscillator coupled to an optical parametric amplifier. The light beams are directed at a particular area on the article under test. A visible light camera, a visible light second harmonic generation camera, an infrared camera, an infrared second harmonic generation camera and a sum-frequency camera are aligned to receive light from the infrared light source and first visible light source reflected from the outer surface of the article under test. Each of the cameras has a filter system that passes only light of a predetermined frequency to an associated one of the cameras. Next, it is determined whether a spectral response of signals from each of the cameras differs from a baseline spectral response. Finally, a fault signal indicating that contamination exists on the outer surface of the article under test is generated when the spectral response of signals from each of the cameras differs from the baseline spectral response.

In a further embodiment, a light beam may be generated from a second visible light source. The second visible light source may be directed at the particular area on the article under test. A third-order camera may be aligned to receive light from the first visible light source and the second visible light source reflected from the outer surface of the article under test. It may be determined whether a spectral response of signals from the third-order camera differs from a baseline spectral response. The third-order camera may have an associated filter system that passes only light of a predetermined frequency to the third-order camera; Finally, a fault signal may be generated indicating that contamination exists on the outer surface of the article under test when the spectral response of signals from the third-order camera differs from the baseline spectral response.

The features, functions, and advantages that have been discussed can be achieved independently in various embodiments or may be combined in yet other embodiments, further details of which can be seen with reference to the following description and drawings.

BRIEF DESCRIPTION OF THE DRAWINGS

The following detailed description, given by way of example and not intended to limit the present disclosure solely thereto, will best be understood in conjunction with the accompanying drawings in which.

DETAILED DESCRIPTION

In the present disclosure, like reference numbers refer to like elements throughout the drawings, which illustrate various exemplary embodiments of the present disclosure.

Figure 1:
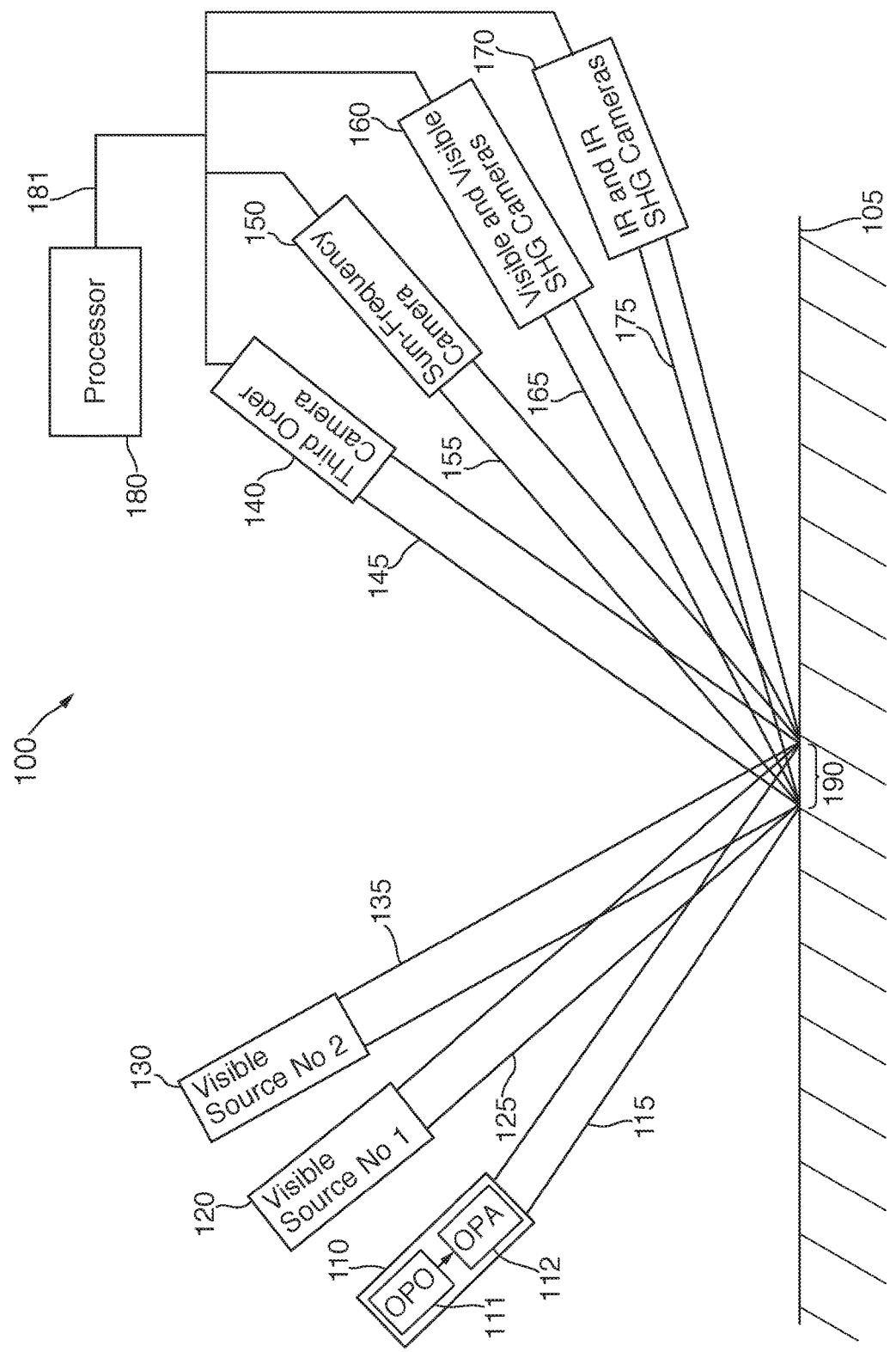
FIG. 1 is a block diagram of an active real-time characterization system for use in monitoring for the presence of contaminants on a surface of a part according to an aspect of the present disclosure.

Referring now to FIG. 1, the active real-time characterization system 100 of the present disclosure includes an infrared (IR) light source 110, a first visible light source 120 and a second visible light source 130. The infrared light source 110 is formed from an optical parametric oscillator (OPO) 111 that is coupled to an optical parametric amplifier (OPA) 112. Each of the light sources 110, 120, 130 is positioned to controllably direct a beam of coherent light at an area 190 on a surface 105 of an article under test, e.g., a part potentially having a contaminant on an upper (exposed) surface thereof. In particular, infrared (IR) source 110 is positioned to controllably direct a beam of coherent light 115 at area 190, first visible light source 120 is positioned to controllably direct a beam 125 of coherent light at area 190, and send visible light source 130 is positioned to controllably direct a beam 135 of coherent light at area 190. The beams 115, 125, 135 may be emitted directly from the respective light sources 110, 120, 130 or may be emitted via respective optical fibers (and appropriate lenses, etc.) coupled to the light sources 110, 120, 130. When beams 115, 125, 135 are emitted via respective optical fibers, each light source 110, 120 130 consists of a laser of the appropriate type (visible or IR light) that is coupled to an input of an associated optical fiber via input optics. The laser is preferably a solid state laser or a diode laser and may be, for example, a pulsed diode laser, a continuous-wave diode laser, a pulsed solid state laser, a continuous-wave solid state laser, a flash-lamp pumped solid state laser, or a diode pumped solid state laser. The input optics consist of an input polarizer, an input wavelength discriminator, an input spatial filter and an input propagation optics. The input polarizer is, for example, a Brewster angle polarizer, a thin film polarizer, a Glan-air or Glan-Thompson polarizer or other crystal polarizer. The wavelength discriminator is, for example, a color filter, a dielectric film, a holographic transmission filter, or a grating. The input propagation optics is formed of one or more refractive or reflective optics which, when used in combination, control the divergence or convergence of the beam as it propagates towards the first input optical fiber. The input optics are optimized for the wavelength of the associated optical source. Coupling optics are coupled to an output of each optical fiber to direct the beam to area 190. IR light source 110 is configured to output light at variable infrared wavelengths based on the use of optical parametric oscillator 111 and optical parametric amplifier 112. Because surface characterization is based on nonlinear optical processing, high peak power is required (i.e., short pulses of infrared light). The combination of an optical parametric oscillator 111 and optical parametric amplifier 112 produces high peak power tunable infrared pulses of a short duration produced using nonlinear optical principles. First visible light source 120 is configured to output light at a first fixed, predetermined visible wavelength and second visible light source 130 is configured to output light at a second fixed, predetermined visible wavelength, different from the first fixed, predetermined visible wavelength.

Figure 2:
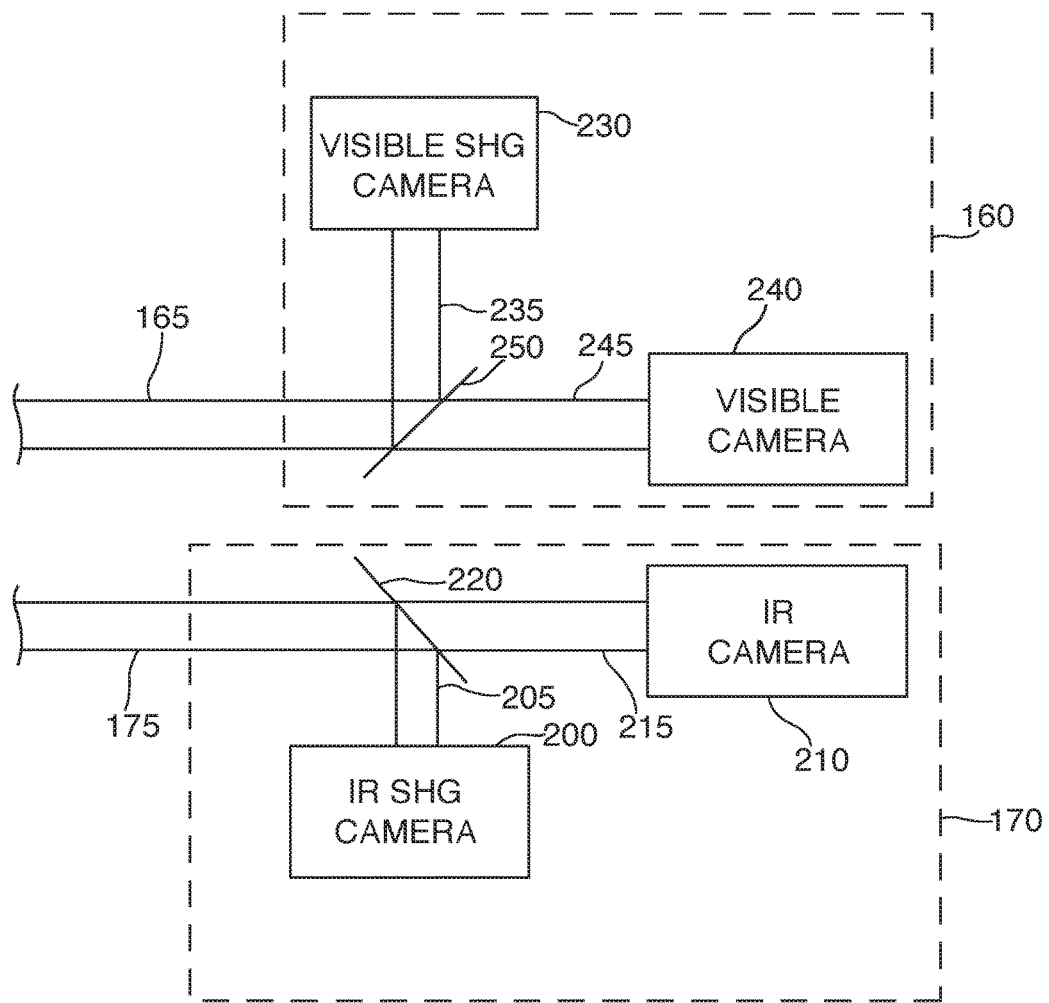
FIG. 2 is a block diagram showing the composition of the infrared light and visible light camera systems according to an aspect of the present disclosure.

System 100 in FIG. 1 also includes a number of cameras for detecting light reflected from the surface 105 of the article under test, including a Raman (third-order) camera 140 which receives a light beam 145 and a sum-frequency camera 150 which receives a light beam 155. System 100 also includes paired visible and visible second harmonic generation (SHG) cameras 160 which receive a light beam 165, and paired IR and IR SHG cameras 170 which receive a light beam 175. Referring now to FIG. 2, the paired visible light and visible light second harmonic generation (SHG) cameras 160 include a visible light SHG camera 230 and a visible light camera 240 which are positioned to each receive light beam 165 via a beam splitter 250. In particular, beam splitter 250 is positioned to split light beam 165 into a first portion 235 that is provided to visible light SHG camera 230 and a second portion 245 that is provided to visible light camera 240. Similarly, the paired IR and IR second harmonic generation (SHG) cameras 170 include an IR SHG camera 200 and an IR camera 210 which are positioned to each receive light beam 175 via a beam splitter 220. In particular, beam splitter 220 is positioned to split light beam 175 into a first portion 205 that is provided to IR SHG camera 200 and a second portion 215 that is provided to IR camera 210. Each of the cameras 140, 150, 200, 210, 230 and 240 produces an output signal that is communicated in a conventional manner to a processor 180 in FIG. 1 via a link 181 for processing as discussed below. As also discussed below, the reflected light beams 145, 155, 165 and 175 are at a particular angle with respect to the surface 105 of the article under test based on the fixed angles that light beams 115, 125 and 135 are directed at the surface 105 of the article under test. The cameras 140, 150, 200, 210, 230 and 240 are thus positioned to receive such light beams. Each camera 140, 150, 200, 210, 230, 240 is a conventional detector as defined below with respect to FIG. 4.

As one of ordinary skill in the art will readily recognize, light sources 110, 120, 130 and cameras 140, 150, 200, 210, 230 and 240 may be fixed in place and the article under test may be moved so that the area 190 of the light beams 115, 125, 135 moves over the entire surface 105 of the article under test. In another embodiment, light sources 110, 120, 130 and cameras 140, 150, 200, 210, 230 and 240 may be mounted on a fixture that moves along the surface 105 of the article under test. In yet another embodiment, light sources 110, 120, 130 may be arranged to raster the respective output light beams 115, 125, 135 across the surface 105 of the article under test, and the cameras 140, 150, 200, 210, 230 and 240 arranged to move proportionally to receive the respective associated return light beams 145, 155, 165, 175.

Figure 3:
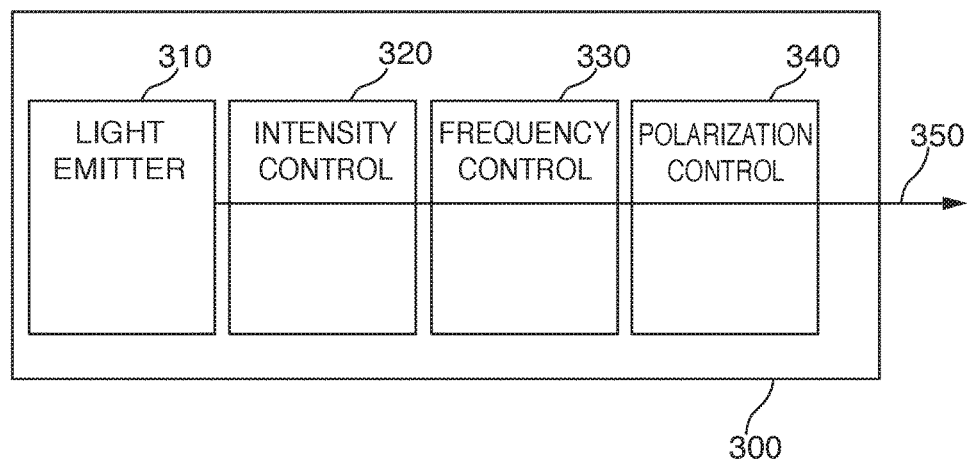
FIG. 3 is a block diagram showing the composition of the visible light sources according to an aspect of the present disclosure.

Referring now to FIG. 3, each of the light sources 120, 130 is configured similarly, as shown by representative light source 300, but each may be configured for a different intensity, frequency and/or polarization. Light source 300 includes a light emitter 310, an intensity control 320, a frequency control 330 and a polarization control 340 for outputting a light beam 350. Light emitter 310 is preferably a narrow frequency bandwidth visible pulse laser and, may be, for example a pulsed diode laser, a continuous wave diode laser or a pulsed solid state laser or a continuous wave solid state laser. Intensity controls may include broadband filters for reducing intensity or may specifically refer to certain frequency notch filters which are intended to drop intensity levels where the cameras can act in a linear fashion. Frequency controls can be accomplished in simple cases by frequency dependent color filters or notch filters and in more elaborate by a spectrophotometer that is typically composed of a diffraction grating which operates at a frequency or bandwidth of interest. The key point for the frequency control is to ensure that only light in beam 350 is directed at the surface 105 and that stray light produced by light emitter 310 is removed, and as one of ordinary skill in the art will readily recognize, other frequency selective elements may also be used. Polarization control typically consists of two separate optical elements, a polarizer which only passes light of one polarization and a polarization modifying element—typically a halfway plate or a quarter wave plate. A halfway plate is used to rotate the polarization to the desired orientation. A quarter wave plate is used to change the polarization from linear to circular or from circular to linear as needed. As shown, the polarizer is the last element before light beam 350 leaves the source and heads for the surface 105. Each light source 120, 130 is configured, based on the selection of light emitter 310, intensity control 320, frequency control 330 and polarization control 340 in each to provide a respective beam 125, 135 of coherent light.

Figure 4:
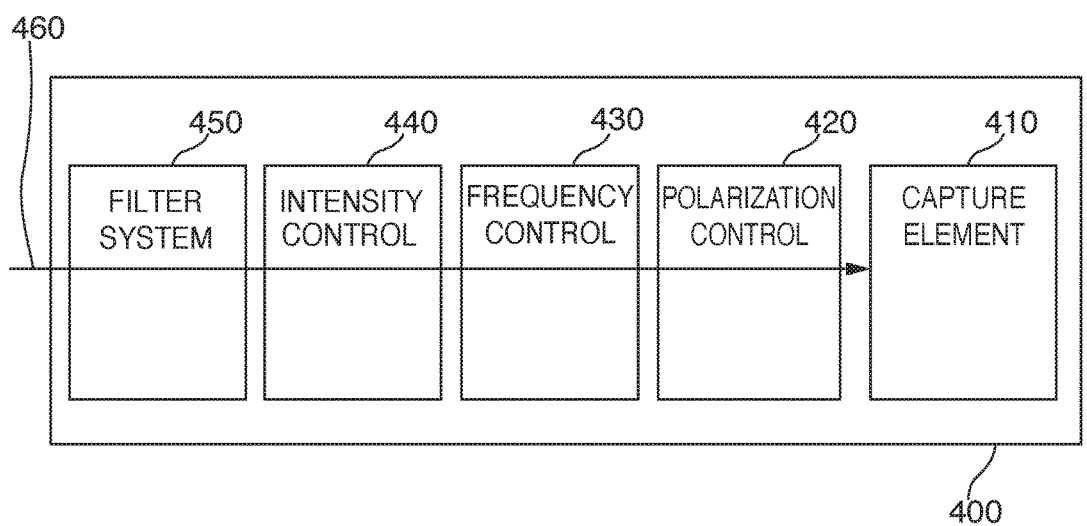
FIG. 4 is a block diagram showing the composition of the cameras according to an aspect of the present disclosure.

Referring now to FIG. 4, each of the cameras 140, 150, 200, 210, 230 and 240 includes elements similar to the elements included in light sources 120, 130, as shown by representative camera 400. Camera 400 includes a capture element 410, a polarization control 420, a frequency control 430 and an intensity control 440 for receiving light beam 460. Exemplary capture elements 34 include, without limitation, cameras, charge-coupled devices, imaging arrays, photometers, and like devices. The frequency control 430 and intensity control 440 operate on light beam 460 in a similar manner as intensity control 320 and frequency control 330 operate on light beam 350 as discussed above. Preferably, polarization control 420 consists of a half wave plate and quarter wave combination, followed by a polarizer. However, as shown by representative camera 400, each of the cameras 140, 150, 200, 210, 230 and 240 also includes a filter system 450 for filtering out certain unwanted features of the reflected light beams 145, 155, 165, 175 before such light beams reach the associated detectors (e.g., the capture element 410 shown in FIG. 4). Filter system 450 may include spectral filters, bandwidth filters, color filters, and/or a spectrometer. In particular, each of the cameras 140, 150, 200, 210, 230 and 240 has a particular signal frequency of interest and the separate filter system 450 included on each of such cameras 140, 150, 200, 210, 230 and 240 ensures that only light at that particular signal frequency of interest is received. The filter system 450 for IR SHG camera 200 is tuned to the frequency of light output by IR light source 110, rejecting all other frequencies. The filter system 450 for IR SHG camera 200 is tuned to the second harmonic frequency of the light output by IR light source 110, rejecting all other frequencies. The filter system 450 for visible light SHG camera 230 is tuned to the frequency of light output by first visible light source 120, rejecting all other frequencies. The filter system 450 for the visible camera 240 is tuned to the second harmonic frequency of the light output by first visible light source 120, rejecting all other frequencies. The filter system 450 for sum-frequency camera 150 is tuned to the sum of the frequency of light output by IR light source 110 and the frequency of light output by first visible light source 120, rejecting all other frequencies. The filter system 450 for third-order camera 140 is tuned to the sum of twice the frequency of light output by first visible light source 120 and the frequency of light output by second visible light source 130, rejecting all other frequencies. The use of filter system 450 in each camera 140, 150, 200, 210, 230 and 240 ensures that the response signals measured by the associated detectors are extremely sensitive to a chemical state of all of the materials at the surface 105 of the article under test. If any particulates or thin films are present, the response signals will show large changes in the spectral response due to the electronic and vibrational resonances of such materials. The inherent surface sensitivity allows for the precise identification and characterization of any surface contaminants, allowing the level of surface contamination to be characterized in a quantitative fashion.

In operation, the system 100 shown in FIG. 1 provides a combination of linear infrared spectroscopy, second order surface frequency mixing spectroscopy, and third-order non-linear optics (e.g., Raman spectroscopy) spectroscopy. System 100 provides a number of ways of performing species identification and allows the cross correlation between the three types of spectroscopies in order to avoid false negative spectral features.

In particular, visible light source 120 and IR light source 110 are configured and positioned to provide light signals which allow the processor 180 to generate simultaneous linear (same frequency) and non-linear (second harmonic generation) real time spectroscopic signals, in conjunction with paired visible light and visible light second harmonic generation (SHG) cameras 160 and paired IR and IR SHG cameras 170. As one of ordinary skill in the art will readily recognize, paired visible light and visible light second harmonic generation (SHG) cameras 160 and paired IR and IR SHG cameras 170 are positioned at a particular predetermined angle to receive the appropriate respective return light beams 165, 175 from surface 105.

Further, visible light source 120 and IR light source 110 are also configured and positioned to provide light signals which allow the processor 180 to generate a sum-frequency ($\omega_{IR}+\omega_{VISIBLE}$) real-time spectroscopic signal, in conjunction with sum-frequency camera 150. As one of ordinary skill in the art will readily recognize, sum-frequency camera 140 is positioned at a particular predetermined angle to receive the appropriate return light beams 155 from surface 105.

Finally, visible light source 120 and visible light source 130 are configured and positioned to provide light signals which allow the processor 180 to generate a third-order ($2\omega_{VIS1}-\omega_{VIS2}$) (e.g., Raman) real-time spectroscopic signal, in conjunction with Raman (third-order) camera 140. As one of ordinary skill in the art will readily recognize, Raman (third-order) camera 140 is positioned at a particular predetermined angle to receive the appropriate return light beams 145 from surface 105.

Processor 180 is coupled to receive signals from each of cameras 140, 150, 200, 210, 230 and 240 and is configured to calculate in real time a linear spectroscopic signal, a second harmonic generation spectroscopic signal, a sum-frequency spectroscopic signal and a third-order spectroscopic signal. The processor 180 is also configured to compare each calculated signal with each other calculated signal and with a predetermined baseline signal to ensure that the article under test conforms to an expected value (e.g., having a particular spectral response). When the processor 180 determines that the calculated signals indicate that the article under test does not conform to the expected value (e.g., the calculated signals show a large change in spectral response), processor 180 may provide a fault signal indicating that the article under test has contamination on an outer surface thereof.

Figure 5:
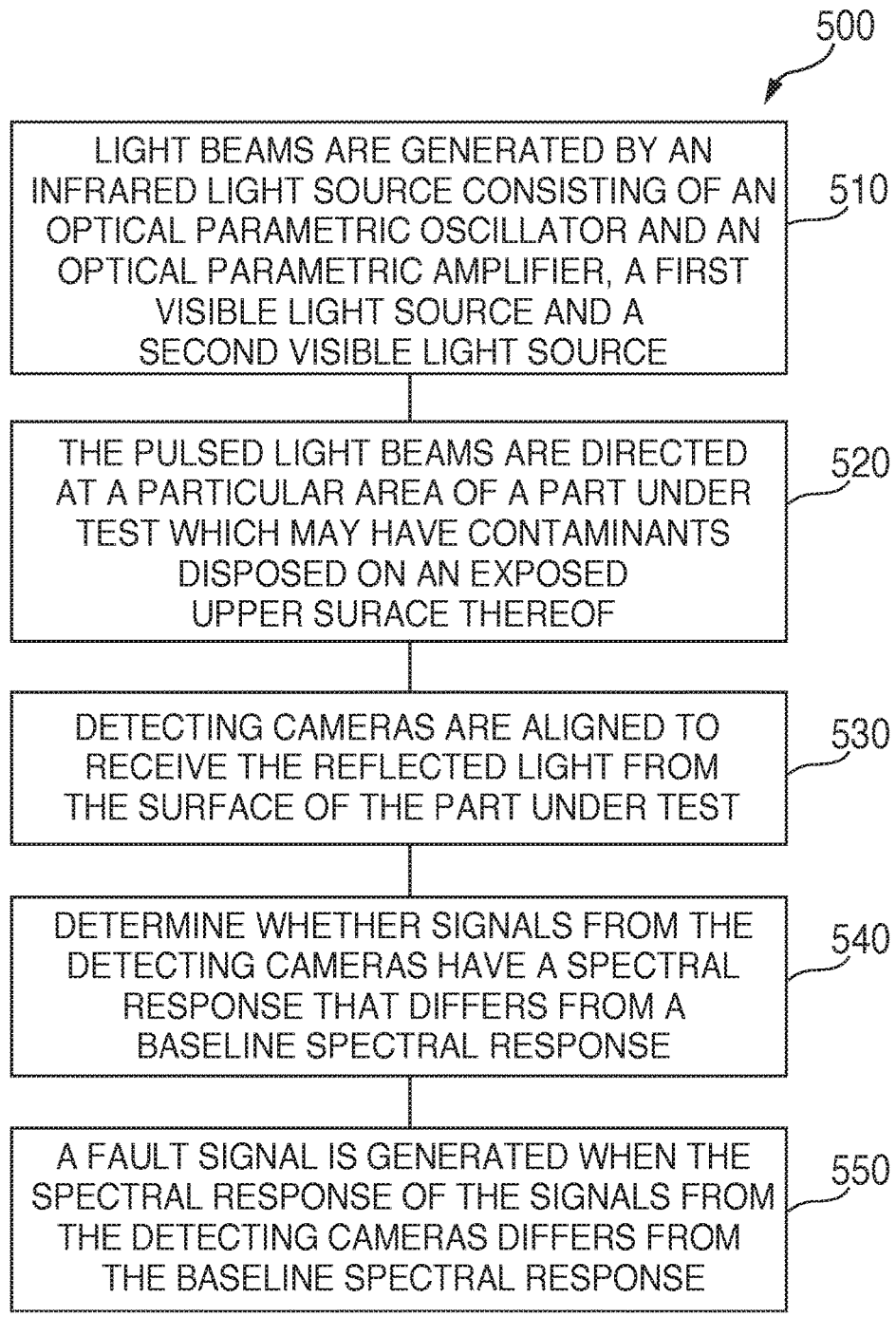
FIG. 5 is a flow chart of a method for operating the active real-time characterization system of the present disclosure.

Referring now to FIG. 5, a flow chart 500 of a method for operating the active real-time characterization system of the present disclosure is shown. In step 510, light beams are generated by an infrared light source consisting of an optical parametric oscillator and an optical parametric amplifier, a first visible light source, and a second visible light source. Next, at step 520, the generated light beams are directed at a particular area of a part under test which may have contaminants disposed on an exposed upper surface thereof. Thereafter, at step 530, detecting cameras are aligned to receive the reflected light from the surface of the part under test, each of the detecting cameras including a filtering system (i.e., the filtering system 450 discussed above with respect to FIG. 4) which filters the received light signal before the received light signal reaches the detector within the detecting camera. Next, at step 540, signals from the detecting cameras are examined to determine whether the spectral response thereof differs from a baseline spectral response. Thereafter, at step 550, a fault signal is generated when the spectral response of the signals from the detecting cameras differs from the baseline spectral response.

Although the present disclosure has been particularly shown and described with reference to the preferred embodiments and various aspects thereof, it will be appreciated by those of ordinary skill in the art that various changes and modifications may be made without departing from the spirit and scope of the disclosure. It is intended that the appended claims be interpreted as including the embodiments described herein, the alternatives mentioned above, and all equivalents thereto.

What is claimed is:

1. An active real-time characterization system for identifying the presence of contaminants on an outer surface of an article under test, comprising:
    an infrared light source for outputting a beam of coherent infrared light, the infrared light source comprising an optical parametric oscillator coupled to an optical parametric amplifier, the infrared light source configured to direct the beam of coherent infrared light at a particular area on the article under test;
    a first visible light source for outputting a first beam of coherent visible light, the first visible light source configured to direct the first beam of coherent visible light at the same particular area on the article under test;
    a visible light camera and a visible light second harmonic generation camera, the visible light camera and the visible light second harmonic generation camera each configured to receive a first predetermined return beam of light from the particular area on the article under test, each of the visible light camera and the visible light second harmonic generation camera having an associated filter system that passes only light of a predetermined frequency to an associated one of the visible light camera and the visible light second harmonic generation camera;
an infrared camera and an infrared second harmonic generation camera, the infrared camera and the infrared second harmonic generation camera each configured to receive a second predetermined return beam of light from the particular area on the article under test, each of the infrared camera and the infrared second harmonic generation camera having an associated filter system that passes only light of a predetermined frequency to an associated one of the infrared camera and the infrared second harmonic generation camera;
a sum-frequency camera configured to receive a third return beam of light from the particular area on the article under test, the sum-frequency camera having an associated filter system that passes only light of a predetermined frequency to the sum-frequency camera; and
a processor coupled to receive first signals from the visible light camera, the visible light second harmonic generation camera, the infrared camera, the infrared second harmonic generation camera and the sum-frequency camera, the processor configured to process the first signals to determine whether the first signals correspond to a spectral response that is different from a baseline spectral response thereby indicating that contaminants exist on the outer surface of the article under test.

2. The active real-time characterization system of claim 1, further comprising:
a second visible light source for outputting a second beam of coherent visible light, the second visible light source configured to direct the second beam of coherent visible light at the same particular area on the article under test;
a third-order camera configured to receive a fourth return beam of light from the particular area on the article under test, the third-order camera having an associated filter system that passes only light of a predetermined frequency to the third-order camera; and
wherein the processor is configured to receive second signals from the third-order camera and to process the second signals from the third-order camera in addition to the first signals from the visible light camera, the visible light second harmonic generation camera, the infrared camera, the infrared second harmonic generation camera and the sum-frequency camera to determine the spectral response.

3. The active real-time characterization system of claim 1, wherein the infrared light source and the first visible light source each includes an intensity control for setting a predetermined intensity for a respective output beam of coherent light.

4. The active real-time characterization system of claim 1, wherein the infrared light source and the first visible light source each includes a frequency control for setting a predetermined wavelength for a respective output beam of coherent light.

5. The active real-time characterization system of claim 1, wherein the infrared light source and the first visible light source each includes a polarization control for setting a predetermined polarization for a respective output beam of coherent light.

6. The active real-time characterization system of claim 1, wherein each of the visible light camera, the visible light second harmonics generation camera, infrared camera, the infrared second harmonic generation camera, and the sum-frequency camera includes a capture element and includes an intensity control to filter a respective input beam of light directed towards the capture element to adjust an intensity of the respective input beam of light.

7. The active real-time characterization system of claim 1, wherein each of the visible light camera, the visible light second harmonics generation camera, infrared camera, the infrared second harmonic generation camera, and the sum-frequency camera includes a capture element and includes a frequency control to filter a respective input beam of light directed towards the capture element to adjust an wavelength of the respective input beam of light.

8. The active real-time characterization system of claim 1, wherein each of the visible light camera, the visible light second harmonics generation camera, infrared camera, the infrared second harmonic generation camera, and the sum-frequency camera includes a capture element and includes a polarization control to filter a respective input beam of light directed towards the capture element to adjust a polarization of the respective input beam of light.

9. The active real-time characterization system of claim 1, further comprising a beam splitter configured to split a return beam of light into two portions and to direct a first portion to the visible light camera and a second portion to the visible light second harmonic generation camera.

10. An active real-time characterization system for identifying the presence of contaminants on an outer surface of an article under test, comprising:
an infrared light source for outputting a beam of coherent infrared light, the infrared light source comprising an optical parametric oscillator coupled to an optical parametric amplifier, the infrared light source configured to direct the beam of coherent infrared light at a particular area on the article under test;
a first visible light source for outputting a first beam of coherent visible light, the first visible light source configured to direct the first beam of coherent visible light at the same particular area on the article under test;
a visible light camera and a visible light second harmonic generation camera, the visible light camera and the visible light second harmonic generation camera each configured to receive a first predetermined return beam of light from the same particular area on the article under test, each of the visible light camera and the visible light second harmonic generation camera having an associated filter system that passes only light of a predetermined frequency to an associated one of the visible light camera and the visible light second harmonic generation camera;
an infrared camera and an infrared second harmonic generation camera, the infrared camera and the infrared second harmonic generation camera each configured to receive a second predetermined return beam of light from the same particular area on the article under test, each of the infrared camera and the infrared second harmonic generation camera having an associated filter system that passes only light of a predetermined frequency to an associated one of the infrared camera and the infrared second harmonic generation camera; and
a processor coupled to receive first signals from the visible light camera, the visible light second harmonic generation camera, the infrared camera, and the infrared second harmonic generation camera, the processor configured to process the first signals to determine whether the first signals correspond to a spectral response that is different from a baseline spectral response thereby indicating that contaminants exist on the outer surface of the article under test.

11. The active real-time characterization system of claim 10, further comprising:
- a second visible light source for controllably outputting a second beam of coherent visible light, the second visible light source configured to direct the second beam of coherent visible light at the same particular area on the article under test;
- a sum-frequency camera configured to receive a fourth return beam of light from the particular area on the article under test, the sum-frequency camera having an associated filter system that passes only light of a predetermined frequency to the sum-frequency camera; and
- wherein the processor is configured to receive second signals from the sum-frequency camera and to process the second signals from the sum-frequency camera in addition to the first signals from the visible light camera, the visible light second harmonic generation camera, the infrared camera, and the infrared second harmonic generation camera to determine the spectral response.

12. The active real-time characterization system of claim 10, wherein the infrared light source and the first visible light source each includes an intensity control for setting a predetermined intensity for a respective output beam of coherent light.

13. The active real-time characterization system of claim 10, wherein the infrared light source and the first visible light source each includes a frequency control for setting a predetermined wavelength for a respective output beam of coherent light.

14. The active real-time characterization system of claim 10, wherein the infrared light source and the first visible light source each includes a polarization control for setting a predetermined polarization for a respective output beam of coherent light.

15. The active real-time characterization system of claim 10, wherein each of the visible light camera, the visible light second harmonics generation camera, infrared camera, the infrared second harmonic generation camera, and the sum-frequency camera includes a capture element and includes an intensity control to filter a respective input beam of light directed towards the capture element to adjust an intensity of the respective input beam of light.

16. The active real-time characterization system of claim 10, wherein each of the visible light camera, the visible light second harmonics generation camera, infrared camera, the infrared second harmonic generation camera, and the sum-frequency camera includes a capture element and a frequency control to filter a respective input beam of light directed towards the capture element to adjust an wavelength of the respective input beam of light.

17. The active real-time characterization system of claim 10, wherein each of the visible light camera, the visible light second harmonics generation camera, infrared camera, the infrared second harmonic generation camera, and the sum-frequency camera includes a capture element and a polarization control to filter a respective input beam of light directed towards the capture element to adjust a polarization of the respective input beam of light.

18. The active real-time characterization system of claim 10, further comprising a beam splitter configured to split a return beam of light into two portions and to direct a first portion to the visible light camera and a second portion to the visible light second harmonic generation camera.

19. A method for identifying the presence of contaminants on to an outer surface of an article under test, the method comprising:
- generating light beams from a first visible light source and an infrared light source, the infrared light source comprising an optical parametric oscillator coupled to an optical parametric amplifier;
- directing the light beams at a particular area on the article under test;
- receiving at, a visible light camera, a visible light second harmonic generation camera, an infrared camera, an infrared second harmonic generation camera, and a sum-frequency camera, light from the infrared light source and light from the first visible light source reflected from the outer surface of the article under test, the visible light camera, the visible light second harmonics generation camera, infrared camera, the infrared second harmonic generation camera, and the sum-frequency camera each having an associated filter system that passes only light of a predetermined frequency to an associated camera;
- determining whether a spectral response corresponding to signals from the visible light camera, the visible light second harmonics generation camera, infrared camera, the infrared second harmonic generation camera, and the sum-frequency camera differs from a baseline spectral response; and
- generating a fault signal indicating that contamination exists on the outer surface of the article under test when the spectral response corresponding to the signals from the visible light camera, the visible light second harmonics generation camera, infrared camera, the infrared second harmonic generation camera, and the sum-frequency camera differs from the baseline spectral response.

20. The method of claim 19, further comprising:
- directing a light beam from a second visible light source at the particular area on the article under test;
- receiving, at a third-order camera, light from the first visible light source and light from the second visible light source reflected from the outer surface of the article under test; and
- determining whether a spectral response corresponding to signals from the third-order camera differs from the baseline spectral response, the third-order camera having an associated filter system that passes only light of a predetermined frequency to the third-order camera wherein the fault signal is generated when the spectral response corresponding to signals from the third-order camera differs from the baseline spectral response.

* * * * *